United States Patent [19]

Nudenberg et al.

[11] 3,940,396

[45] Feb. 24, 1976

[54] 1,2,3,4,4A,5,7,7A-OCTAHYDROTHIENO[3,4-B]PYRAZINES 6,6-DIOXIDES

[75] Inventors: Walter Nudenberg, West Caldwell, N.J.; Edward L. Hagen, Woodbury, Conn.; Julian R. Little, Hendersonville, N.C.; Chung-Ling Mao, Sandy Hook, Conn.

[73] Assignee: Uniroyal Inc., New York, N.Y.

[22] Filed: Feb. 28, 1973

[21] Appl. No.: 336,590

[52] U.S. Cl. 260/268 BC; 260/268 FT; 260/75 TN; 260/2.5 A; 260/77.5 AP
[51] Int. Cl.² .................................. C07D 295/10
[58] Field of Search .............. 260/268 BC, 268 FT

[56] References Cited
UNITED STATES PATENTS

| | | | |
|---|---|---|---|
| 3,663,548 | 5/1972 | Nitta et al. | 260/268 R |
| 3,723,476 | 3/1973 | Nakanishi et al. | 260/347.7 |
| 3,808,212 | 4/1974 | Renth et al. | 260/268 SY |

*Primary Examiner*—R. Gallagher
*Assistant Examiner*—Jose Tovar
*Attorney, Agent, or Firm*—Willard R. Sprowls

[57] ABSTRACT

Disclosed are new chemical compounds namely 1,4-dialkanols of octahydrothieno[3,4-b]pyrazine 6,6-dioxides and 4-alkanols of octahydrothieno[3,4-b]pyrazine 6,6-dioxides, the use of such compounds in the production of polyurethanes, and methods of making such compounds.

24 Claims, No Drawings

1,2,3,4,4A,5,7,7A-OCTAHYDROTHIENO[3,4-B]PYRAZINES, 6,6-DIOXIDES

CROSS-REFERENCE TO RELATED APPLICATION

Copending application Ser. No. 336,752 filed of even date herewith, now U.S. Pat. No. 3,882,122, in the name of applicant Hagen, discloses and claims the 1,2,3,4,4a,5,7,7a-octahydrothieno [3,4-b]pyrazine 6,6-dioxides and the 1,2,3,4,4a,5,7,7a-octahydro-2-alkyl-thieno[3,4-b]pyrazine 6,6-dioxides which are disclosed herein.

Copending application Ser. No. 336,842 filed of even date herewith in the names of applicant Mao, et al., now U.S. Pat. No. 3,821,132 issued June 28, 1974 is directed to the preparation of polyurethane forms by the use of the diols and the aminoalcohols disclosed herein in combination.

FIELD OF THE INVENTION

The invention in one aspect comprises the new class of chemical compounds, 1,4-dialkanoloctahydrothieno [3,4-b]pyrazine 6,6-dioxides having the general formula:

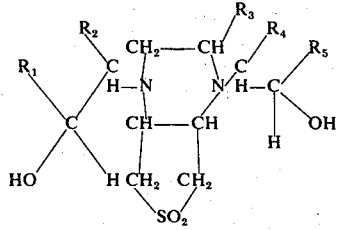

wherein $R_1$ and $R_5$ may be the same or different and each represents a hydrogen atom, an alkyl group having 1 to 10 carbon atoms, an aryl group, a substituted aryl group, an alkoxyalkyl group, a bis-alkoxymethyl group, a cyanoalkyloxymethyl group or a sulfolanyl-methyl group, $R_2$ and $R_4$ may be the same or different and each represents a hydrogen atom, or a lower alkyl group having 1 to 5 carbon atoms, and $R_1$ together with $R_2$ and/or $R_4$ together with $R_5$ can constitute an alkylene group having 1 to 4 carbon atoms, and $R_3$ may be a hydrogen atom or an alkyl group having 1 to 10 carbon atoms.

The heterocyclic dialkanols of the invention are useful as chain extenders for polyurethane elastomers which have a unique combination of physical properties such as transparency, low durometer, high tensile strength and high tear resistance. Chain extenders are low molecular weight diols which have the effect of concentrating the rigid diisocyanate molecules at intervals along the polymer chain. These diols also provide long pot life to liquid polyurethane mixes which facilitates the handling and fabrication of articles of cast or liquid-coated articles made from polyurethanes. The pot life is the time interval between completeness of mixing and the time at which the viscosity increases to the point where the mixture cannot be worked.

In another aspect the invention comprises the new class of chemical compounds 4-alkanoloctahydro-thieno[3,4-b]pyrazine 6,6-dioxides having the general formula:

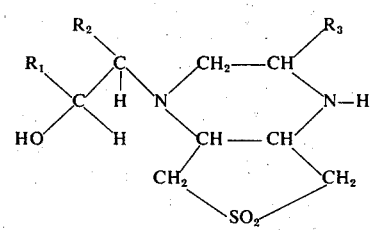

wherein $R_1$, $R_2$ and $R_3$ as defined above.

In a further aspect, the invention relates to use of the chemical compounds disclosed above as chain extenders or promoters in the preparation of polyurethanes.

In a still further aspect, the invention comprises methods of synthesizing such compounds.

DESCRIPTION OF THE PRIOR ART

The prior art compounds which are the most closely related to the compounds of this invention are the 1,4-piperazine dialcohols having the general formula:

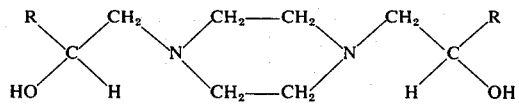

wherein R may be hydrogen or a lower alkyl group having 1 to 5 carbon atoms. Several prior art references discuss the use of these compounds as chain extenders for polyurethane syntheses. The 1,4-piperazine dialkanols are not suitable as chain extenders for the "one shot" system of polyurethane systhesis because the "pot life" of the mixture of diisocyanate, polyester or polyether diol and these low molecular weight piperazine dialkanols is too short at processing temperatures. Apparently the two tertiary amino groups exert a strong accelerating effect on the rate of reaction between diisocyanate and diol.

DETAILED DESCRIPTION OF THE INVENTION INCLUDING PREFERRED EMBODIMENTS

The novel compounds of this invention are made by a two step synthesis. The first step involves the formation of an intermediate thienopyrazine dioxide II or III according to the following reaction scheme:

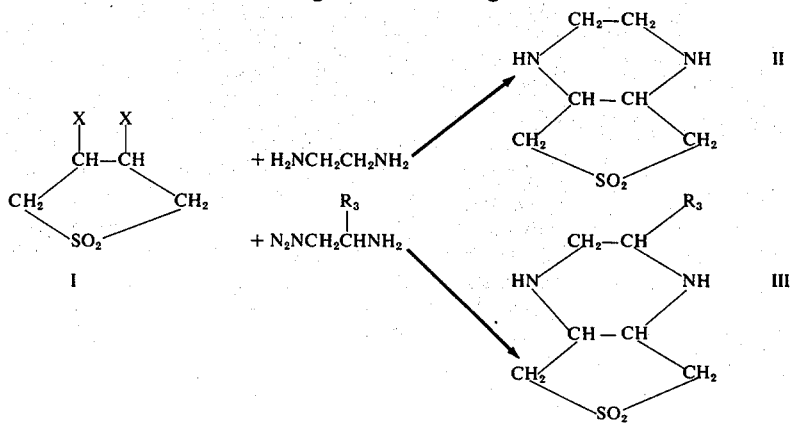

In the foregoing reaction scheme X is halogen (usually chlorine or bromine although other halogens are equally useful) and $R_3$ is hydrogen or alkyl having 1 to 10 carbon atoms. In this reaction, the atarting material I, a 3,4-dihalotetrahydrothiophene 1,1-dioxide, is reacted with excess ethylene diamine to form intermediate cyclic diamine II which is 1,2,3,4,4a,5,7,7a-octahydrothieno-[3,4-b]pyrazine 6,6-dioxide. Intermediate cyclic diamine III, 1,2,3,4,4a,5,7,7a-octahydro-2-alkylthieno[3,4-b]pyrazine 6,6-dioxide is formed when an excess of a C-alkyl substituted ethylene diamine such as propylene diamine is reacted with the 3,4-dihalotetrahydrothiophene 1,1-dioxide. The usual procedure is to dissolve reactant I in a suitable solvent such as dioxane and add the resultant solution to an excess of diamine in dioxane solution. The reaction solution is kept at less than 70° to 80°C. By the time the reaction is complete, two layers will have formed, the top layer containing intermediate diamine II or III and the bottom layer containing the diamine salt and excess diamine. At least three equivalents of diamine must be used since two equivalents are required to dehydrohalogenate the 3,4-dihalotetrahydrothiophene 1,1-dioxide. The amount of solvent used is not critical as long as enough is used to dissolve the 3,4-dihalotetrahydrothiophene 1,1-dioxide I. The reaction temperature is also not critical but the exotherm must be controlled by either the rate of addition of reactant I or by the external cooling.

The second step involves the formation of the diols, types IV and V of this invention, by reaction of intermediate compound II or III with an excess of an epoxide according to the following scheme:

The systematic names for the compounds of this invention, IV and V, are as follows:
IV. (wherein $R_3$ is hydrogen); 1,2,3,4,4a,5,7,7a-octahydrothieno[3,4-b]-1,4-dialkanolpyrazine 6,6-dioxide, and
V. (wherein $R_3$ is an alkyl group); 1,2,3,4,a,5,7,7a-octahydro-2-alkylthieno[3,4-b]-1,4-dialkanolpyrazine 6,6-dioxide.

Any epoxide wherein the epoxy group is an oxirane group is suitable to prepare the diols of this invention. Outstanding results are obtained with ethylene oxide and monosubstituted ethylene oxides having the formula

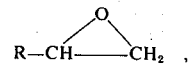

where R is a hydrocarbon radical such as alkyl with 1 to 10 carbon atoms, aryl, alkyl substituted aryl or cycloalkyl. Exemplary of such epoxides are ethylene oxide, propylene oxide, 1-butene oxide, 2-butene oxides, 1-hexene oxide, 1-octene oxide and substituted alkylene oxides such as cyclohexene oxide, styrene oxide; glycidyl ethers, such as methyl glycidyl ether, ethyl glycidyl ether, hexyl glycidyl ether, phenyl glycidyl ether, o, m, or p-tolyl glycidyl ether, o, m, or p-chlorophenyl glycidyl ether; and unsaturated epoxides, such as vinyl cyclohexene monoxide, butadiene monoxide, methallyl glycidyl ether, o, m, p-allylphenyl glycidyl ether and allyl glycidyl ether. Halogen-containing epoxides may also be used. Exemplary of such halogen-containing epoxides are epichlorohydrin, epibromohydrin, epi-

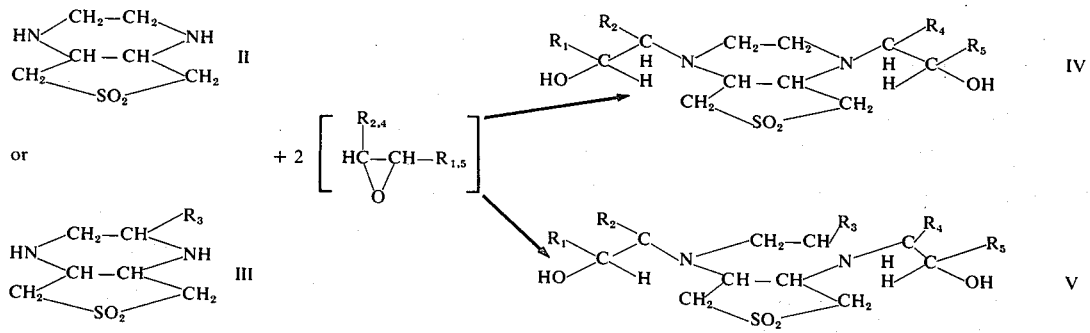

In this reaction the diols of this invention are formed by reacting the pyrazine dioxides II and III in water with an excess of a suitable expoxide. In general, one mole of the pyrazine dioxide is reacted with 2.5 moles of the epoxide. Some of the reactions exhibit an exotherm while others require heating to reflux for complete reaction. In the case where the epoxide is not completely miscible with water, the reaction mixture becomes homogeneous as the reaction proceeds. Reaction times and temperatures will vary depending upon the epoxide and some reactions will require use of a co-solvent in conjunction with water. Suitable co-solvents are dioxane and acetone.

fluorohydrin, trifluoromethyl ethylene oxide. Also suitable are the acetal- and ketal-containing epoxides such as 1,1-dimethoxy-2,3-epoxypropane, 1,1-diethoxy-2,3-epoxypropane, 2-(2,3-epoxypropoxy)-tetrahydropyran; sulfone-containing epoxides such as 7-oxa-3-thiabicyclo[4.1.0]heptane 3,3-dioxide and nitrile-containing epoxides such as B-cyanoethyl glycidyl ether. Other exemplary epoxides are shown in the working examples given below.

Another class of novel difunctional compounds, which are related to compounds of types IV and V disclosed above and are useful in the preparation of polyurethanes, particularly as promoters for the chain extension reaction in preparation of polyurethanes, have the following general formula:

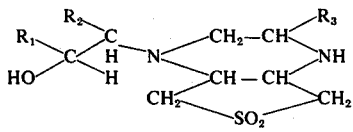

wherein $R_1$, $R_2$ and $R_3$ are as defined above. These are referred to hereinafter as type VI compounds.

These novel type VI compounds are made by (a) reacting only one equivalent of an epoxide to one mole of intermediate compound II or III or (b) reacting one mole of intermediate compound III with more than one mole of an epoxide which has a bulky side group under mild conditions. In the latter case the bulky side group of the epoxide favors (because of steric factors) the mono addition away from the alkyl group in the 3-position of the pyrazine ring. The systematic name for this new class of aminoalcohols is 1,2,3,4,4a,5,7,7a-octahydro-2-alkylthieno[3,4-b]-pyrazine-1-monool 6,6-dioxide. These aminoalcohols, like the dialcohols of this invention, are useful in preparing polyurethanes. Because of their basic nature, they are valuable promoters for the chain extending (polymerization) reaction, especially when used in conjunction with the diols of types IV and V.

Example 1

This example illustrates the preparation and evidence of structure of a type II diamine which can be used as an intermediate in the syntheses of the novel compounds of this invention.

A solution of 567 g. (3 moles) of 3,4-dichlorotetrahydrothiophene 1,1-dioxide in 2000 ml. of dioxane was added while stirring over a period of three hours at 0°C. to a solution of 1330 ml. (20 moles) of ethylene diamine in 1500 ml. of dioxane. After the addition was complete, the reaction mixture was heated on a steam bath for 2½ hours and kept at ambient temperature while stirring overnight. The mixture separated into two layers. The top layer contained a major portion of the product diamine. The bottom layer, containing excess unreacted ethylene diamine and the amine salt, was washed twice with 1000 ml. of dioxane and all the dioxane portions were than combined. The dioxane was stripped off leaving the crude product. Three recrystallizations from toluene produced 203 g. (40%) of 1,2,3,4,4a,5,7,7a-octahydrothieno[3,4-b]pyrazine 6,6-dioxide, M.P. 112.5°–114°C. IR showed bands at 3340 cm$^{-1}$, 3310 cm$^{-1}$ (NH), and at 1290 cm$^{-1}$ and 1100 cm$^{-1}$ (SO$_2$). NMR in D$_2$O showed bands with relative areas of 2:2:1 consistent with the II structure.

Analysis — Calcd. for C$_6$H$_{12}$N$_2$O$_2$S (percent): C, 40.8; H, 6.82; N, 15.9; S, 18.2. Found (percent): C, 41.2; H, 6.92; N, 15.6; S, 18.3.

Example 2

The procedure for preparing type III diamines is the same as the procedure of Example 1 for preparing type II diamines. In this case, using the same thiophene dioxide and substituting propylene diamine for the ethylene diamine, the white crystalline product, 1,2,3,4,4a,5,7,7a-octahydro-2-methylthieno[3,4-b]pyrazine 6,6-dioxide, had a melting point of 152°–156°C. IR spectrum showed absorptions at 3300 cm$^{-1}$ (NH) and at 1290 cm$^{-1}$ and 1115 cm$^{-1}$ (SO$_2$).

Analysis — Calcd. for C$_7$H$_{14}$N$_2$O$_2$S (percent): C, 44.2; H, 7.37; N, 14.7; S, 16.8. Found (percent): C, 44.17; H, 7.35; N, 14.76; S, 16.65.

Example 3a

This example illustrates the preparation of a typical diol of this invention using a reactive, watersoluble epoxide. (Water soluble epoxides have at most four carbon atoms). 2.5 ml. (0.05 mole) of ethylene oxide was condensed into a reaction flask and dissolved in 5 ml. of water. To this solution was added gradually at room temperature, a solution of 3.5 g. (0.02 mole) in 5 ml. of water of 1,2,3,4,4a,5,7,7a-octahydrothieno[3,4-b]pyrazine 6,6-dioxide, the diamine of Example 1. After the reaction was complete, the reaction mixture was allowed to cool to room temperature and the waterr and excess epoxide were removed under vacuum, leaving a white solid. Trituration with toluene gave a product, 1,2,3,4,4a,5,7,7a-octahydrothieno[3,4-b]pyrazine 1,4-diethanol 6,6-dioxide, M.P. 145°–147°C. IR spectrum showed bands at 3300 cm$^{-1}$, broad (OH) at 1285 cm$^{-1}$ and 1125 cm$^{-1}$ (SO$_2$) and at 1010 cm$^{-1}$ (CO).

Analysis — Calcd. for C$_{10}$H$_{20}$N$_2$O$_4$S (percent): C, 45.41; H, 7.58; N, 10.6; S, 12.1. Found (percent): C, 45.34; H, 7.35; N, 10.45; S, 11.8.

Example 3b

Example 3a was repeated using the diamine of Example 1 but substituting propylene oxide for the ethylene oxide. The resultant product, 1,2,3,4,4a,5,7,7a-octahydrothieno[3,4-b]pyrazine-1,4-bis(α-methylethanol) 6,6-dioxide was a viscous liquid that became semisolid on standing. The IR spectrum showed absorptions at 3450 cm$^{-1}$ (OH) and at 1300 and 1120 cm$^{-1}$ (SO$_2$).

NMR showed a doublet for the methyl groups at 1.15 ppm (J = 6 Hz) with fine triplet splitting. The ratio of methyl hydrogens to all other hydrogens was found to be 1:3.3 (calculated 1:3.0).

Hydroxyl number — Calcd. 385. Found 387.
Analysis — Calcd. for C$_{12}$H$_{24}$N$_2$O$_4$S (percent): C, 49.3; H, 8.22; N, 9.59; S, 10.95. Found (percent): C, 47.8; H, 7.91; N, 9.34; S, 10.65.

Example 3c

Example 3a was repeated using the diamine of Example 1 and substituting isobutylene oxide for the ethylene oxide. The resultant product 1,2,3,4,4a,5,7,7a-octahydrothieno[3,4-b]pyrazine-1,4-bis(α,α-dimethylethanol) 6,6-dioxide had a M.P. of 70°–85°C. The IR spectrum showed absorptions at 3550 cm$^{-1}$ (OH) and at 1300 and 1110 cm$^{-1}$ (SO$_2$).

NMR showed two methyl singlets, unequal in intensity, indicative of two different geometrical isomers being present. The relatively broad melting point range also indicates this. NMR ratio of methyl hydrogens to all others was found to be 1:1.27 calculated 1:1.33.

Analysis — Calcd. for C$_{14}$H$_{28}$N$_2$O$_4$S (percent): C, 52.5; H, 8.75; N, 8.75; S, 10.0. Found (percent): C, 52.3; H, 8.93; N, 7.59; S, 9.31.

Example 3d

Example 3a was repeated using the diamine of Example 1 and substituting 2,3-epoxy-1-propanol (glycidol) for ethylene oxide. The resultant product, 1,2,3,4,4a,5-7,7a-octahydrothieno[3,4-b]pyrazine-1,4-bis(α- hydroxymethylethanol) 6,6-dioxide, had a M.P. 260°C. (dec) and was very hygroscopic. The IR spectrum showed absorptions at 3400 cm$^{-1}$ (OH), strong, and at 1280 and 1130 cm$^{-1}$ (SO$_2$).

Hydroxyl number — Calcd. 693. Found 727.

NMR was complex but gave a ratio of hydrogens on carbon α to nitrogen to all other hydrogens of 0.64:1; calculated 0.67:1. The fact that this diol was hygroscopic made elemental analysis meaningless and complicated other analyses.

Example 3e

Example 3a was repeated using the diamine of Example 1 and substituting 3,3-dimethoxypropylene oxide for ethylene oxide. The resultant product, 1,2,3,4-4a,5,7,7a-octahydrothieno[3,4-b]pyrazine-1,4-bis(2-hydroxypropionaldehydedimethylacetal) 6,6-dioxide was a viscous liquid. The IR spectrum showed absorptions at 3570 cm$^{-1}$ (OH) and at 1300 cm$^{-1}$ and 1120 cm$^{-1}$ (SO$_2$).

Analysis — Calcd. for $C_{16}H_{32}N_2O_8S$ (percent): C, 46.6; H, 7.77; N, 6.79; S, 7.76. Found (percent): C, 45.5; H, 7.78; N, 6.60; S, 7.74.

Example 3f

Example 3a was repeated using the diamine of Example 1 and substituting 3-methoxypropylene oxide for ethylene oxide. The resultant product, 1,2,3,4,4a-5,7,7a-octahydrothieno[3,4-b]pyrazine-1,4-bis(3-methoxy-2-propanol 6,6-dioxide, was a viscous liquid. The IR spectrum showed absorptions at 3510 cm$^{-1}$ (OH) and at 1290 cm$^{-1}$ and 1115 cm$^{-1}$ (SO$_2$).

Analysis — Calcd. for $C_{14}H_{28}N_2O_6S$ (percent): C, 47.7; H, 7.96; N, 7.95; S, 9.10. Found (percent): C, 47.03; H, 8.06; N, 7.96; S, 9.41.

Example 3g

Example 3a was repeated using the diamine of Example 2 and a water-soluble epoxide, ethylene oxide. The resultant product 1,2,3,4,4a,5,7,7a-octahydro-2-methylthieno[3,4-b]pyrazine-1,4-diethanol 6,6-dioxide was a viscous liquid. IR showed OH (3430 cm$^{-1}$) and SO$_2$ (1300 and 1120 cm$^{-1}$).

NMR gave two doublets for the methyl group at 1.10 ppm indicative of two geometrical isomers. The ratio of methyl hydrogens to all others was found to be 1:7.0, calculated 1:6.3.

Analysis — Calcd. for $C_{11}H_{22}N_2O_4S$ (percent): C, 47.5; H, 7.97; N, 10.1; S, 11.5. Found (percent): C, 47.33; H, 8.23; N, 10.20; S, 11.68.

Example 3h

Example 3g was repeated substituting propylene oxide for ethylene oxide. The resultant product, 1,2,3,4,4a,5,7,7a-octahydro-2-methylthieno[3,4-b]pyrazine-1,4-bis(α-methylethanol) 6,6-dioxide, was a viscous liquid. The IR spectrum showed absorptions at 3520 cm$^{-1}$ (OH) and at 1300 cm$^{-1}$ and 1120 cm$^{-1}$ (SO$_2$).

NMR gave a ratio of methyl hydrogens to all other hydrogens 0.49:1; calculated 0.53:1.

Analysis — Calcd. for $C_{13}H_{26}N_2O_4S$ (percent): C, 50.96; H, 8.55; N, 9.15; S, 10.43. Found (percent): C, 49.69; H, 8,34; N, 9.07; S, 10.39.

Example 3i

Example 3e was repeated substituting the diamine of Example 2 for the diamine of Example 1. The resultant product, 1,2,3,4,4a,5,7,7a-octahydro-2-methyl-thieno[3,4b]-pyrazine-1,4-bis(2-hydroxypropional-dehydedimethylacetal) 6,6-dioxide was a viscous liquid. The IR spectrum showed absorptions at 3510 cm$^{-1}$ (OH) and at 1300 cm$^{-1}$ and 1150 cm$^{-1}$ (SO$_2$).

Analysis — Calcd. for $C_{17}H_{34}N_2O_8S$ (percent): C 47.9; H, 8.0; N, 6.57; S, 7.5. Found (percent): C, 47.03; H, 8.39; N, 6.35; S, 7.18.

Example 3j

Example 3a was repeated using the diamine of Example 2 and reacting it with 3-(β-cyanoethoxy)propylene oxide. The resultant product, 3,3'-[1,2,3,4,4a-5,7,7a-octahydro-2-methylthieno[3,4-b]pyrazine-1,4-bis[3"λ"-(2-hydroxypropoxy)-propionitrile]] 6,6-dioxide was a viscous liquid. The IR spectrum showed absorptions at 3510 cm$^{-1}$ (OH), 2240 cm$^{-1}$ (CN) and at 1300 cm$^{-1}$ and 1100 cm$^{-1}$ (SO$_2$).

Analysis — Calcd. for $C_{19}H_{32}N_4O_6S$ (percent): C, 51.3; H, 7.2; N, 12.6; S, 7.2. Found (percent): C, 50.86; H, 7.15; N, 12.32; S, 6.4.

Example 4a

This example illustrates the preparation and evidence of structure of a typical compound of this invention, 1,2,3,4,4a,5,7,7a-octahydrothieno[3,4-b]pyrazine-1,4-bis(α-phenylethanol) 6,6-dioxide using styrene oxide, an epoxide which is water insoluble.

15 g. (0.12 mole) of styrene oxide was added to a solution of 8.8 g. (0.05 mole) of 1,2,3,4,4a,5,7,7a-octahydrothieno[3,4-b]pyrazine 6,6-dioxide in 50 ml. of water and 100 ml. of acetone. The reaction mixture was refluxed overnight after which the solvents and excess epoxide were removed under vacuum leaving behind a hard, glassy solid, 1,2,3,4,4a,5,7,7a-octahydrothieno[3,4-b]pyrazine-1,4-bis(α-phenylethanol) 6,6-dioxide, M.P. 56°-63°C. IR showed absorptions at 3500 cm$^{-1}$ (OH), 3050 cm$^{-1}$, 1600 cm$^{-1}$ and 760 cm$^{-1}$ (phenyl), 1290 cm$^{-1}$ and 1110 cm$^{-1}$ (SO$_2$).

Hydroxyl number — Calcd. 269; Found 264.

Analysis — Calcd. for $C_{22}H_{28}N_2O_4S$ (percent): C, 63.5; H, 6.73; N, 6.73; S, 7.69 Found (percent): C, 62.78; H, 6.88; N, 6.96; S, 8.31.

Example 4b

Example 4a was repeated using 1,2-octene oxide in place of styrene oxide. The resultant product, 1,2,3,4-4a,5,7,7a-octahydrothieno[3,4-b]pyrazine-1,4-bis(α-hexylethanol) 6,6-dioxide, was a viscous liquid that became paste-like on standing. The IR spectrum showed absorptions at 3550 cm$^{-1}$ (OH) and 1290 cm$^{-1}$ and 1120 cm$^{-1}$ (SO$_2$).

NMR was complex but gave ratio of hexyl hydrogens to all other hydrogens in D$_2$O of 1.4:1; calculated 1.33:1.

Analysis — Calcd. for $C_{22}H_{28}N_2O_4S$ (percent): C, 61.2; H, 10.2; N, 6.48; S, 7.42. found (percent): C, 58.58; H, 10.09; N, 7.07; S, 8.16.

Example 4c

Example 4a was repeated using cyclohexene oxide in place of styrene oxide and dioxane in place of acetone. The resultant product, 1,2,3,4,4a,5,7,7a-octahydro-thieno[3,4-b]pyrazine-1,4-bis(2-cyclohexanol) 6,6-dioxide, had a M.P. of 249°–250.5°C., recrystallized from ethanol/water. The IR spectrum showed absorptions at 3500 cm$^{-1}$ (OH) and 1290 cm$^{-1}$ and 1120 cm$^{-1}$ (SO$_2$).

NMR gave ratio of cyclohexyl methylene hydrogens to all others of 1.01:1; calculated 1:1.

Analysis — Calcd. for $C_{18}H_{32}N_2O_4S$ (percent): C, 58.1; H, 8.61; N, 7.53; S, 8.61. Found (percent): C, 58.3; H, 8.44; N, 7.60; S, 8.95.

Example 4d

Example 4a was repeated using 2,3-butene oxide in place of styrene oxide and acetone as a co-solvent. The resultant product, 1,2,3,4,4a,5,7,7a-octahydrothieno[3,4-b]pyrazine-1,4-bis($\alpha,\beta$-dimethylethanol) 6,6-dioxide, was a white solid isomeric mixture, M.P. 100°–115°C. The IR spectrum showed absorptions at 3450 cm$^{-1}$ (OH) and 1290 cm$^{-1}$ and 1120 cm$^{-1}$ ($SO_2$).

NMR gave a ratio of methyl hydrogens to all others of 1:1.5; calculated 1:1.33.

Analysis — Calcd. for $C_{14}H_{28}N_2O_4S$ (percent): C, 52.5; H, 8.75; N, 8.75; S, 10.0. Found (percent): C, 49.93; H, 8.69; N, 8.46; S, 9.29.

Example 4e

Example 4a was repeated using butadiene monoxide in place of styrene oxide. The resultant product, 1,2,3,4,4a,5,7,7a-octahydrothieno[3,4-b]pyrazine-1,4-bis($\alpha$-vinylethanol) 6,6-dioxide, was a viscous liquid. The IR spectrum showed absorptions at 3500 cm$^{-1}$ (OH), 1290 cm$^{-1}$ and 1110 cm$^{-1}$ ($SO_2$), 3100 cm$^{-1}$, 1630 cm$^{-1}$, 995 cm$^{-1}$ and 920 cm$^{-1}$ (vinyl).

NMR gave a ratio of non-olefinic hydrogen to olefinic hydrogen of 3.4:1; calculated 3.0:1.

Analysis — Calcd. for $C_{14}H_{24}N_2O_4S$ (percent): C, 53.2; H, 8.87; N, 8.87; S, 10.1. Found (percent): C, 51.3; H, 7.67; N, 8.83; S, 9.79.

Example 4f

Example 4d was repeated using 1,2-butene oxide in place of styrene oxide. The resultant product, 1,2,3,4,4a,5,7,7a-octahydrothieno[3,4-b]pyrazine-1,4-bis($\alpha$-ethylethanol) 6,6-dioxide, was a viscous liquid. The IR spectrum showed absorptions at 3500 cm$^{-1}$ (OH) and 1290 cm$^{-1}$ and 1110 cm$^{-1}$ ($SO_2$).

NMR gave a ratio of ethyl hydrogens to all other of 0.55:1; calculated 0.55:1.

Analysis — Calcd. for $C_{14}H_{28}N_2O_4S$ (percent): C, 52.5; H, 8.75; S, 10.0; N, 8.75 Found (percent): C, 52.51; H, 8.65; N, 8.65; S, 9.58.

Examples 5a, 5b and 5c illustrate the preparation of mixed diols (types IV and V) of the present invention by the reaction of two different epoxides in sequence with diamines of types II and III above. It is preferred to react with only one epoxide at a time because this enables better control of the reaction and of the structure of the product than would be possible using two different epoxides at the same time.

Example 5a

This example illustrates the preparation of still another typical compound of this invention, one in which two different epoxides are reacted with a type II diamine made according to Example 1.

To a solution of 88 g. (0.5 mole) of 1,2,3,4,4a-5,7,7a-octahydrothieno[3,4-b]pyrazine 6,6-dioxide in 200 ml. of water was added a solution of 25 g. (0.5 mole) of propylene oxide in 50 ml. of water over a period of one hour. The mixture was stirred at ambient temperature overnight after which a solution of 22 g (0.7 moles) of ethylene oxide in 50 ml. of water was added gradually to the reaction mixture. Three hours after the addition of the ethylene oxide solution was completed, all volatile products, including water, were removed leaving behind a viscous liquid, 1,2,3,4,4a,5,7,7a-octahydrothieno[3,4-b]pyrazine-1-ethanol-4-($\alpha$-methylethanol) 6,6-dioxide. IR spectrum showed the presence of OH and $SO_2$ and NMR gave a ratio of 0.15 for methyl hydrogen to all other hydrogen as against a calculated value of 0.16. The hydroxyl number — Calcd. 403; Found 397.

Example 5b

The procedure of Example 5a was followed except that the type III diamine of Example 2 was first reacted witn 1,2-octene oxide in a 70/30 acetone/water solution, and the resultant aminoalcohol was then further reacted with an excess of ethylene oxide. The resultant product, 1,2,3,4,4a,5,7,7a-octahydro-2-methylthieno[3,4-b]pyrazine-1-ethanol-4-($\alpha$-hexylethanol) 6,6-dioxide was a viscous liquid which became solid on standing. The IR spectrum showed absorptions of 3510 cm$^{-1}$ (OH) and 1300 cm$^{-1}$ and 1110 cm$^{-1}$ ($SO_2$).

Analysis — Calcd. for $C_{17}H_{34}N_2O_4S$ (percent): S, 8.84. Found (percent): S, 9.21. Molecular weight — Calcd. 363; Found 371.

Example 5c

Example 5b was repeated substituting 2,3-epoxy-1-(2-sulfolanyl)butane for 1,2-octene oxide and propylene oxide for the ethylene oxide. The resultant product, 1,2,3,4,4a,5,7,7a-octahydro-2-methylthieno[3,4-b]pyrazine-1-($\alpha$-methylethanol)-4-($\beta$-methyl-$\alpha$-tetrahydro-1,1-dioxo-2-thenyl)ethanol 6,6-dioxide, was a viscous liquid. The IR spectrum showed absorptions at 3530 cm$^{-1}$ (OH) and 1300 cm$^{-1}$ and 1120 cm$^{-1}$ ($SO_2$).

Analysis — Calcd. for $C_{18}H_{34}N_2O_6S_2$ (percent): C, 49.29; H, 7.76; N, 6.39; S, 14.61. Found (percent): C, 49.40; H, 7.70; N, 6.57; S, 14.31.

Example 6a

This example demonstrates the preparation and evidence of structure of a type VI compound. To a solution of 3.8 g (0.02 mole) of 1,2,3,4,4a,5,7,7a-octahydro-2-methylthieno[3,4-b]pyrazine 6,6-dioxide in 50 ml. of water was added a solution of 1.2 g. (0.02 mole) of propylene oxide in 10 ml. of water. The reaction mixture was stirred overnight after which the solvent was removed by vacuum. The reaction product was a white solid, 1,2,3,4,4a,5,7,7a-octahydro-2-methylthieno[3,4-b]pyrazine-4-($\alpha$-methylethanol) 6,6-dioxide, M.P. 121°–124°C. The IR spectrum showed absorptions at 3500 cm$^{-1}$ (OH), 3300 cm$^{-1}$ (NH), 1285 cm$^{-1}$ and 1120 cm$^{-1}$ ($SO_2$).

Analysis — Calcd. for $C_{10}H_{20}N_2O_3S$ (percent): C, 48.36; H, 8.12; N, 11.28; S, 12.91. Found (percent): C, 47.98; H, 8.12; N, 11.52; S, 13.34.

Example 6b

This experiment demonstrates the preparation of another type VI compound. The procedure used was the same as in Example 6a with the exception that 1,2-octene oxide was substituted for propylene oxide. The resultant product, 1,2,3,4,4a,5,7,7a-octahydro-2-methylthieno[3,4-b]pyrazine-4-($\alpha$-hexylethanol) 6,6-dioxide was a viscous liquid which became solid on standing. The IR spectrum showed absorptions at 3510 cm$^{-1}$ (OH), 3300 cm$^{-1}$ (NH) and at 1300 cm$^{-1}$ and 1120 cm$^{-1}$ ($SO_2$).

Analysis — Calcd. for $C_{15}H_{30}N_2O_3S$ (percent): S, 10.06. Found (percent: S, 8.97.
The hydroxyl number — Calcd. 352; Found 333.

Example 6c

This experiment demonstrates the preparation of still another type VI compound. The procedure used was the same as in Example 6a with the exception that 2,3-epoxy-1-(2-sulfolanyl)butane was substituted for propylene oxide. The resultant product, 1,2,3,4,4a,5,7-,7a-octahydro-2-methylthieno[3,4-b]pyrazine-4-($\beta$-methyl-$\alpha$-tetrahydro-1,1-dioxo-2-thenyl)ethanol 6,6-dioxide was a viscous liquid. The IR spectrum showed absorptions at 3580 $cm^{-1}$ (OH), 3350 $cm^{-1}$ (NH) and at 1300 $cm^{-1}$ and 1150 $cm^{-1}$ ($SO_2$).

Example 7a

This example illustrates the preparation and evidence of structure of a diol of this invention made using a type VI aminoalcohol. To a solution of 38 g. (0.1 mole) of 1,2,3,4,4a,5,7,7a-octahydro-2-methylthieno[3,4-b]pyrazine-4-($\beta$-methol-$\alpha$-tetrahydro-1,1-dioxo-2-thenyl)ethanol 6,6-dioxide from Example 6c in 100 ml. of water was added a solution of 7.0 g. (0.12 mole) of propylene oxide in 10 ml. of water. The reaction mixture was stirred at ambient temperature for three days after which the solvent was stripped off under reduced pressure. The resultant diol, 1,2,3,4,4a,5,7,7a-octahydro-2-methylthieno[3,4-b]pyrazine-1-($\alpha$-methylethanol)-4-($\beta62$ -methyl-$\alpha$(tetrahydro-1,1-dioxo-2-thenyl)ethanol 6,6-dioxide, was a viscous liquid and chemically was essentially the same as the product of Example 5c. The IR spectrum showed absorptions at 3500 $cm^{-1}$ broad (OH) and at 1285 $cm^{-1}$ and 1125 $cm^{-1}$ ($SO_2$).

Analysis — Calcd. for $C_{18}H_{34}N_2O_6S_2$ (percent): C, 49.29; H, 7.76; N, 6.39; S, 14.61. Found (percent): C, 49.09; H, 7.44; N, 6.59; S, 14.24.

Example 7b

Following the procedure of Example 7a, 1,2,3,4,4a,5,7,7a-octahydro-2-methylthieno[3,4-b]pyrazine-1-ethanol-4-($\alpha$-hexylethanol) 6,6-dioxide was prepared using as the starting type VI aminoalcohol 1,2,3,4,4a,5,7,7a-octahydro-2-methylthieno[3,4-b]pyrazine-4-($\alpha$-hexylethanol) 6,6-dioxide (0.1 mole) which was reacted with ethylene oxide (0.12 mole). The resultant product, 1,2,3,4,4a,5,7,7a-octahydro-2-methylthieno[3,4-b]pyrazine-1-ethanol-4-($\alpha$-hexylethanol) 6,6-dioxide, was a viscous liquid which became solid on standing and chemically was essentially identical to the product of Example 5b. The IR spectrum showed absorptions at 3510 $cm^{-1}$ (OH), and at 1300 $cm^{-1}$ and 1110 $cm^{-1}$ ($SO_2$).

Example 8

The type IV and V compounds of this invention find use as chain extenders for the one-shot system of solid castable polyurethanes. In this system, the long chain polyol of a type well-known in the art, either a polyester or polyether, and the chain extender (a diol) are mixed without chemical reaction taking place. The polyisocyanate, usually a diisocyanate, is then added and chain extension and crosslinking occur more or less simultaneously. This example demonstrates the use of three typical compounds of this invention as chain extenders in a typical castable polyurethane formulation.

The polyethylene adipate diol* and the chain extenders were mixed in the amounts (grams) shown in Table I in a three-necked glass resin kettle fitted for vacuum and with a motor-driven stirrer. The individual mixtures were degassed by heating and stirring at 100°C. under 5 mm. of pressure for 30 minutes. After cooling to 75°C. a given amount of molten 4-4'-diphenylmethane diisocyanate was rapidly added to the binary mixture, stirred and degassed under vacuum for 2 more minutes. The resultant liquid polyurethane mixture was then poured equally into two open top 7.5 × 7.5 × 0.1 inch Teflon (trademark) coated molds which were heated and kept at 115°C. The "pot life" or the time in minutes was then measured for the mixture to show signs of forming strings when touched with a spatula (incipient gelation). The molds were then closed and the cast samples were cured in a heated hydraulic press using contact pressure for 1.5 hours at 110°C. After cure, the samples were cooled to room temperature, removed from the mold and conditioned in air at 25°C. and 50% relative humidity for 14 days before testing.

*Vibrathane A-112 (trademark), polyethylene adipate diol, molecular weight = 1300, from Uniroyal Chemical.

From the test data shown in Table I, it can be seen that the diols of this invention, unlike the N,N'-bis(2-hydroxypropyl)piperazine (stock X), as chain extenders in one-shot liquid cast polyurethanes produce long "pot life" mixes similar to those from 1,4-butane diol (stock VII) or 1,4-bis($\beta$-hydroxyethoxy)benzene (stocks VIII and IX) making them especially suitable for making either large polyurethane castings or coated fabrics. It is well-known that diamine chain extenders such as 4,4'-diaminodiphenylmethane and 3,3'-dichloro-4,4'-diaminodiphenylmethane produce mixes with "pot life" too short for such uses. It should be noted that the mix with N,N'-bis(2-hydroxypropyl)piperazine (stock X) was mixed at a lower temperature, i.e., at 60°C. in order that a casting could be made when this diol was mixed at 75°C. the mix set up before the three components of the mix could be thoroughly mixed.

It should be especially noted that polyurethane castings made with the type IV and V diols of this invention also show a unique combination of physical properties such as transparency, low durometer, high tensile strength and tear resistance. This combination of properties makes them uniquely suited for polyurethane coated fabrics with a good hand and with superior wear resistance. The commonly used diol chain extenders do not give this combination of properties as shown in stocks VII, VIII, and IX. Not only does the N,N'-bis(2-hydroxypropyl)piperazine impart a prohibitively short "pot life" when used as a chain extender, but also the final elastomer properties are inferior with regard to tear resistance and tensile strength.

Example 9

Liquid cast polyurethanes using the one-shot method of Example 8 were prepared with other representative diols of this invention as chain extenders according to the amounts listed in Table II. As seen from the tabulation of physical properties, these chain extenders also produce mixes with long "pot life" depending inversely on the concentration of chain extender and produce polyurethane elastomers with superior properties depending on the concentration of chain extender used.

While Examples 8 and 9 show the preparation of solid polyurethane products and while the compounds of the invention can be used in making solid polyurethane products generally, for example, molded solid polyurethane articles, composite articles such as polyurethane-coated fabrics embodying a solid polyurethane coating or film on a fabric substrate etc., the compounds can be used in making foamed polyurethane materials. A preferred method of making foamed polyurethanes using a major proportion of a Type IV or a Type V diol and a minor proportion of a Type VI aminoalcohol in combination is the subject of the above-mentioned copending application of Mao et al.

wherein $R_1$ and $R_5$ are the same or different and each represents a hydrogen atom, alkyl group having 1 to 10 carbon atoms, phenyl, hydroxymethyl, alkoxymethyl group having 2 to 7 carbon atoms, dimethoxymethyl, diethoxyethyl, tetrahydropyranoxymethyl, phenoxymethyl, o-, m-, p-toloxymethyl, o, m-, p-allylphenoxymethyl, o-, m-, p-chlorophenoxymethyl, $\beta$-cyanoethoxymethyl or sulfolanylmethyl group, $R_2$ and $R_4$ are the same or different and each represents a hydrogen atom, or lower alkyl group having 1 to 5 carbon atoms, $R_1$ together with $R_2$ or $R_4$ together with $R_5$ constitute a cyclohexylene group, $R_3$ is a hydrogen atom or methyl Table I

| Stock | I | II | III | IV | V | VI | VII | VIII | IX | X |
|---|---|---|---|---|---|---|---|---|---|---|
| Polyethylene adipate | 177* | 164 | 175.4 | 162.2 | 178 | 165 | 195 | 185.4 | 177.6 | 187.8 |
| Example 3b diol | 32.7 | 40.8 | | | | | | | | |
| Example 3h diol | | | 34.2 | 42.8 | | | | | | |
| Example 3g diol | | | | | 31.2 | 38.9 | | | | |
| 1,4-Butane diol | | | | | | | 10.1 | | | |
| 1,4-Bis(hydroxyethoxy)-benzene | | | | | | | | 22.2 | 27.8 | |
| N,N'-Bis(2-hydroxypropyl)-piperazine | | | | | | | | | | 22.6 |
| 4,4'-Diphenylmethane diisocyanate | 70.4 | 75.2 | 70.4 | 74.9 | 71.0 | 75.7 | 75.0 | 72.6 | 75.1 | 69.8 |
| Moles chain extender/1000 g. elastomer | 0.4 | 0.5 | 0.4 | 0.5 | 0.4 | 0.5 | 0.4 | 0.4 | 0.5 | 0.4 |
| "Pot life", Minutes | 12 | 9 | 15 | 11 | 13 | 11 | 13 | 13 | 10 | 2** |
| Durometer, Shore A[1] | 66 | 80 | 66 | 75 | 64 | 71 | 76 | 89 | 93 | 59 |
| Stress at 100% Elong'n., psi[2] | 320 | 760 | 265 | 510 | 330 | 490 | 610 | 1020 | 1360 | 275 |
| Tensile strength, psi[3] | 5880 | 8510 | 5260 | 4660 | 3840 | 3740 | 5590 | 3580 | 3140 | 3360 |
| % Elongation[3] | 480 | 470 | 500 | 390 | 460 | 400 | 640 | 670 | 620 | 470 |
| Tear strength, lbs./in.[4] | 183 | 405 | 151 | 291 | 85 | 118 | 278 | 374 | 314 | 46 |
| Optical properties | TRSP.[5] | TRSP. | TRSP. | TRSP. | TRSL.[6] | TRSL. | OPQ.[7] | OPQ. | OPQ | TRSL. |

*All amounts in grams.
**Mixed at 60°C. "Pot life " less than 1 minute when mixed at 75°C. and gelled before it could be poured into mold.
[1]ASTM D2240-68
[2]From autographic stress-strain measurements. A 0.10" thick sample is died out into a ring, 3 cm. inner diameter, 3.5 cm. outer diameter, placed around pulleys rotating at 200 rpm, and elongated at a rate of 10 in./min. These stress values were determined at 100% elongation.
[3]Scott tensiles following methods ASTM D412-68 and Scott Model L Tester instructions. A jaw separation rate of 20 in./min. and a sample thickness of 0.10" were used.
[4]Following procedure of ASTM 624-54 but using a sample measuring 3" × 1" which was died out from a sheet of stock 0.10" thick with a 2" slit extending lengthwise from one end. The two legs were put in the jaws of a Scott Tester and elongated until torn apart. The force required to accomplish this was recorded.
[5]TRSP = Transparent
[6]TRSL = Translucent
[7]OPQ = Opaque Table II

| Stock | XI | XII | XIII | XIV | XV | XVI | XVII |
|---|---|---|---|---|---|---|---|
| Polyethylene adipate | 82.9 | 66.3 | 82.2 | 90.3 | 74.8 | 76.3 | 92.5 |
| Example 3e diol | 23.1 | | | | | | |
| Example 3f diol | | 10.6 | | | | | |
| Example 3i diol | | | 23.9 | | | | |
| Example 3j diol | | | | 17.9 | | | |
| Example 4a diol | | | | | 29.1 | | |
| Example 5a diol | | | | | | 23.3 | |
| Example 5b diol | | | | | | | 15.2 |
| 4,4'-Diphenylmethane diisocyanate | 34.1 | 23.1 | 33.9 | 31.8 | 36.2 | 40.3 | 32.4 |
| Moles chain extender/1000 g. of elastomer. | 0.4 | 0.3 | 0.4 | 0.3 | 0.5 | 0.6 | 0.3 |
| "Pot life", minutes | 15 | >20 | 20 | 21 | 12 | 7 | 20 |
| Durometer, Shore A | 55 | 44 | 51 | 49 | 90 | 81 | 50 |
| Stress at 100% elong'n., psi | 205 | 135 | 150 | 200 | 570 | 650 | 175 |
| Tensile strength, psi | 2770 | — | 2410 | 2050 | 4390 | 5290 | 2220 |
| % Elongation | 580 | — | 630 | 630 | 410 | 410 | 730 |
| Tear strength, lbs./in. | 121 | 122 | 100 | 76 | 463 | 361 | 99 |
| Optical Properties | TRSP. | TRSP. | TRSP. | TRSP. | TRSP. | TRSP. | TRSP. |

We claim:
1. A compound having the formula:

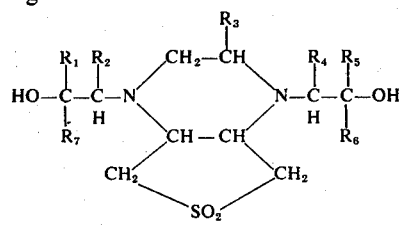

group, and $R_6$ and $R_7$ represent a hydrogen atom or methyl group.

2. A compound having the formula:

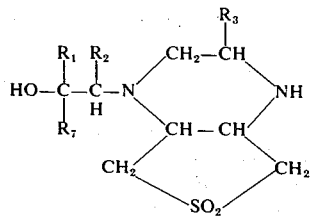

wherein $R_1$ is a hydrogen atom, alkyl group having 1 to 10 carbon atoms, phenyl, hydroxymethyl, alkoxymethyl group having 2 to 7 carbon atoms, dimethoxymethyl, diethoxyethyl, tetrahydropyranoxymethyl, phenoxymethyl, o-, m-, p-toloxymethyl, o-, m-, p-allylphenoxymethyl, o-, m-, p-chlorophenoxymethyl, β-cyanoethoxymethyl or sulfolanylmethyl group, $R_2$ is a hydrogen atom or lower alkyl group having 1 to 5 carbon atoms, $R_1$ together with $R_2$ constitute a cyclohexylene group, $R_3$ is a hydrogen atom or methyl group, and $R_7$ is a hydrogen atom or methyl group.

3. 1,2,3,4,4a,5,7,7a-octahydrothieno[3,4-b]pyrazine-1,4-diethanol 6,6-dioxide.
4. 1,2,3,4,4a,5,7,7a-octahydrothieno[3,4-b]pyrazine-1,4-bis(α-methylethanol) 6,6-dioxide.
5. 1,2,3,4,4a,5,7,7a-octahydrothieno[3,4-b]pyrazine-1,4-bis(α,α-dimethylethanol) 6,6-dioxide.
6. 1,2,3,4,4a,5,7,7a-octahydrothieno[3,4-b]pyrazine-1,4-bis(α-hydroxymethylethanol) 6,6-dioxide.
7. 1,2,3,4,4a,5,7,7a-octahydrothieno[3,4-b]pyrazine-1,4-bis(2-hydroxypropionaldehydedimethylacetal) 6,6-dioxide.
8. 1,2,3,4,4a,5,7,7a-octahydrothieno[3,4-b]pyrazine-1,4-bis(3-methoxy-2-propanol) 6,6-dioxide.
9. 1,2,3,4,4a,5,7,7a-octahydro-2-methylthieno[3,4-b]pyrazine-1,4-diethanol 6,6-dioxide.
10. 1,2,3,4,4a,5,7,7a-octahydro-2-methylthieno[3,4-b]pyrazine-1,4-bis(α-methylethanol) 6,6-dioxide.
11. 1,2,3,4,4a,5,7,7a-octahydro-2-methylthieno[3,4-b]pyrazine-1,4-bis(2-hydroxypropionaldehydedimethylacetal) 6,6-dioxide.
12. 3,3'-[1,2,3,4,4a-5,7,7a-octahydro-2-methylthieno[3,4-b]pyrazine-1,4-bis[3''-(2-hydroxypropoxy)propionitrile]] 6,6-dioxide.
13. 1,2,3,4,4a-5,7,7a-octahydrothieno[3,4-b]pyrazine-1,4-bis(α-hexylethanol) 6,6-dioxide.
14. 1,2,3,4,4a-5,7,7a-octahydrothieno[3,4-b]pyrazine-1,4-bis(2-cyclohexanol) 6,6-dioxide.
15. 1,2,3,4,4a-5,7,7a-octahydrothieno[3,4-b]pyrazine-1,4-bis(α,β-dimethylethanol) 6,6-dioxide.
16. 1,2,3,4,4a-5,7,7a-octahydrothieno[3,4-b]pyrazine-1,4-bis(α-vinylethanol) 6,6-dioxide.
17. 1,2,3,4,4a-5,7,7a-octahydrothieno[3,4-b]pyrazine-1,4-bis(α-ethylethanol) 6,6-dioxide.
18. 1,2,3,4,4a-5,7,7a-octahydrothieno[3,4-b]pyrazine-1-ethanol-4-(α-methylethanol) 6,6-dioxide.
19. 1,2,3,4,4a-5,7,7a-octahydro-2-methylthieno[3,4-b]pyrazine-1-ethanol-4-(α-hexylethanol) 6,6-dioxide.
20. 1,2,3,4,4a-5,7,7a-octahydro-2-methylthieno[3,4-b]pyrazine-1-(α-methylethanol)-4-(β-methyl-α-tetrahydro-1,1-dioxo-2-thenyl)ethanol 6,6-dioxide.
21. 1,2,3,4,4a-5,7,7a-octahydro-2-methylthieno[3,4-b]pyrazine-4-(α-methylethanol) 6,6-dioxide.
22. 1,2,3,4,4a-5,7,7a-octahydro-2-methylthieno[3,4-b]pyrazine-4-(α-hexylethanol) 6,6-dioxide.
23. 1,2,3,4,4a,5,7,7a-octahydrothieno[3,4-b]pyrazine-1,4-bis(α-phenylethanol) 6,6-dioxide.
24. 1,2,3,4,4a,5,7,7a-octahydro-2-methylthieno[3,4-]-pyrazine-4-(β-methyl-α-tetrahydro-1,1-dioxo-2-thenyl)ethanol 6,6-dioxide.

* * * * *

UNITED STATES PATENT OFFICE
CERTIFICATE OF CORRECTION

Patent No. 3,940,396  Dated February 24, 1976

Inventor(s) Walter Nudenberg et al.

It is certified that error appears in the above-identified patent and that said Letters Patent are hereby corrected as shown below:

Column 16, line 35, insert -- b -- at the beginning of the line.

Signed and Sealed this

Eighteenth Day of October 1977

[SEAL]

Attest:

RUTH C. MASON  
Attesting Officer

LUTRELLE F. PARKER  
Acting Commissioner of Patents and Trademarks